US008592770B2

(12) United States Patent
Ben-Zvi et al.

(10) Patent No.: US 8,592,770 B2
(45) Date of Patent: Nov. 26, 2013

(54) METHOD AND APPARATUS FOR DUV TRANSMISSION MAPPING (75) Inventors: Guy Ben-Zvi, Doar Na Misgav (IL); Eitan Zait, Kiriat Tivon (IL); Vladimir J. Dmitriev, Karmiel (IL); Steven M. Labovitz, Sunnyvale, CA (US); Erez Graitzer, Doar Na Misgav (IL); Ofir Sharoni, Shimshit (IL)

(73) Assignee: Carl Zeiss SMS Ltd., Karmiel (IL)

( * ) Notice: Subject to any disclaimer, the term of this patent is extended or adjusted under 35 U.S.C. 154(b) by 0 days.

(21) Appl. No.: 12/281,059

(22) PCT Filed: Jul. 10, 2008

(86) PCT No.: PCT/IL2008/000960
§ 371 (c)(1),
(2), (4) Date: Jan. 18, 2011

(87) PCT Pub. No.: WO2009/007977
PCT Pub. Date: Jan. 15, 2009

(65) Prior Publication Data
US 2011/0101226 A1    May 5, 2011

Related U.S. Application Data (60) Provisional application No. 60/929,783, filed on Jul. 12, 2007, provisional application No. 61/030,093, filed on Feb. 20, 2008.

(51) Int. Cl.
*G01F 23/00* (2006.01)
(52) U.S. Cl.
USPC ...................................... 250/358.1

(58) Field of Classification Search
USPC ...................................... 250/358.1
See application file for complete search history.

(56) References Cited

U.S. PATENT DOCUMENTS 6,133,576 A    10/2000 Shafer et al.
6,184,976 B1 *  2/2001 Park et al. ............... 356/237.4
(Continued)

FOREIGN PATENT DOCUMENTS

JP    11-095410       4/1999
JP    2000/019271     1/2000
JP    2000/048953     2/2000
JP    2006-350352    12/2006

OTHER PUBLICATIONS

Wang et al., "Study of CaF2 samples using DUV birefringence measurement and x-ray diffraction techniques," 2007, SPIE Proceedings, vol. 6682, pp. 668210-668210-7.*

(Continued)

*Primary Examiner* — Kiho Kim
(74) *Attorney, Agent, or Firm* — Pearl Cohen Zedek Latzer Baratz, LLP (57) ABSTRACT

Apparatus and method for transmittance mapping of an object which is at least partially transparent to deep ultraviolet radiation. The method comprises directing a wide-band deep ultraviolet radiation so as to illuminate different areas of an array of successive areas of the object; using an optical detector positioned on an opposite side of the object with respect to the radiation source detecting the wide-band deep ultraviolet radiation that emerges from the object; and processing signals from the optical detector to determine the transmittance of the radiation through the different areas of the array of successive areas of the object.

12 Claims, 7 Drawing Sheets

(56) References Cited

U.S. PATENT DOCUMENTS

| | | | |
|---|---|---|---|
| 6,372,392 B1* | 4/2002 | Hoshino et al. | 430/5 |
| 6,587,262 B1 | 7/2003 | Fujiwara et al. | |
| 6,614,520 B1 | 9/2003 | Bareket et al. | |
| 6,727,025 B1 | 4/2004 | Shiraishi | |
| 7,042,577 B1* | 5/2006 | Jacob et al. | 356/511 |
| 7,123,356 B1 | 10/2006 | Stokowski et al. | |
| 7,251,033 B1 | 7/2007 | Phan et al. | |
| 2001/0021845 A1* | 9/2001 | Lai | 606/5 |
| 2002/0171825 A1 | 11/2002 | Krantz et al. | |
| 2003/0133113 A1* | 7/2003 | Hajduk et al. | 356/367 |
| 2004/0207836 A1 | 10/2004 | Chhibber et al. | |
| 2004/0223145 A1* | 11/2004 | Butt et al. | 356/237.5 |
| 2005/0084767 A1 | 4/2005 | Zait et al. | |
| 2006/0234144 A1 | 10/2006 | Watson et al. | |
| 2007/0019187 A1 | 1/2007 | Schuster et al. | |
| 2007/0019856 A1 | 1/2007 | Furman et al. | |
| 2010/0007888 A1* | 1/2010 | Glover | 356/436 |
| 2010/0086212 A1* | 4/2010 | Buck et al. | 382/195 |

OTHER PUBLICATIONS

International Search Report from PCT/IL2008/000960 mailed on Apr. 15, 2009.

S.Shimada et al. in "A new model of haze generation and storage life-time estimation for masks", BACUS news, Apr. 2007, vol. 23, issue 4.

Tchikoulaeva et al. in "ACLV Degradation: Root Cause Analysis and Effective Monitoring Strategy", Photomask and Next-Generation Lithography Mask Technology XV. Edited by Horiuchi, Toshiyuki. Proceedings of the SPIE, vol. 7028, pp. 702816-702816-10, Jun. 2008.

Jong Min Kim et al. in "Threshold residual ion concentration on photo-mask surface to prevent haze defects", Photomask and Next-Generation Lithography Mask Technology XIV. Edited by Watanabe, Hidehiro. Proceedings of the SPIE, vol. 6607, pp. 66071Z, May 2007.

Office Action for Korean Application No. 10-2010-7003147, mailed on Feb. 25, 2013.

Ben-Zvi G et al. "Very high sensitivity mask transmittance mapping and measurements based on non imaging optics with Galileo (TM)" SPIE Proceeding, The International Society for Optical Engineering—SPEI, Bellinham, Wahsington, USA, vol. 7028, Apr. 18, 2008, pp. 702828-1-10, XP002645912, ISSN: 0277-786X, DOI: 10.1117/12.798462.

Ben-Zvi G et al. "Very high sensitivity mask DUV transmittance mapping and measurements based on non imaging optics" SPIE Proceeding, The International Society for Optical Engineering—SPEI, Bellinham, Wahsington, USA, vol. 6792, Jan. 21, 2008, pp. 679213-1-11, XP002523397, ISSN: 0277-786X, DOI: 10.1117/12.798801.

\* cited by examiner

METHOD AND APPARATUS FOR DUV TRANSMISSION MAPPING

CROSS-REFERENCE TO RELATED APPLICATIONS

This application is a National Phase Application of PCT International Application Number PCT/IL2008/000960, International filing date Jul. 10, 2008, Entitled "Method and Apparatus for Duv Transmission Mapping", which claims priority of U.S. Provisional Patent Application No. 60/929,783, Entitled "Method and Apparatus for Early Detection and Mapping of Haze Layer Growth on Reticles", filed Jul. 12, 2007 and U.S. Provisional Patent Application No. 61/030,093, Entitled "Method and Apparatus for Duv Transmission Mapping of Photomasks and their Coatings", filed Feb. 20, 2008, all of which are incorporated herein by refernce in their entirety.

FIELD OF THE INVENTION

The present invention relates to transmission mapping. More particularly, the present invention relates to a method and apparatus for the mapping of deep ultraviolet (DUV) transmission of an object that is at least partially transparent to DUV.

BACKGROUND OF THE INVENTION

Photomasks used in the photolithography process for manufacturing integrated circuits (IC) are exposed to high levels of irradiance by deep ultraviolet (DUV) radiation, also known as actinic wavelength radiation. In recent years, a number of side-effects of the photolithography process at actinic wavelengths have been discovered, notably the degradation of photomask quality as a function of time and cumulative exposure. A common phenomenon is the growth of defects on mask surfaces, even when the masks were defect free when they were shipped from the mask supplier.

The mechanisms for progressive degradation of photomask quality are numerous. A partial list of the causes of degradation includes: growth of chemical contaminants on the photomask and on lens surfaces (often referred to as haze), chrome ion migration, modification of the photomask surface and bulk due to accumulated exposure to DUV radiation, and numerous other causes. Contaminants may form on the pellicle of the photomask, between the pellicle and the patterned mask, or on the mask itself. Contaminants on the mask may form on the photomask coating (e.g. chrome coatings, MoSi coatings), or on clear areas of the quartz substrate (pattern or scribe lines). The IC industry traditionally refers to the substrate material as glass or quartz, although it is typically made of fused silica.

Photomask transmission and phase changes that affect light passing through the photomask under some types of progressive degradation processes can be either positive or negative. Transmission can either increase or decrease, when no absorption is involved, as a result of optical thin-film effects or modifications of surface and bulk material properties. It is well known in the field of thin films optics that if a transparent thin film is deposited on a transparent substrate (such as, for example, glass), a change of reflection and transmission may result. For example, if the thickness of a film is one quarter of the wavelength of the incident radiation and the index of refraction of the film equals to the square-root of the index of the glass substrate, then reflection will drop to zero at normal incidence and transmission will increase by 4%-5%. When the value of the index of refraction value is not exactly the square root of the index of the substrate, or the thickness is less then a quarter of the wavelength, the transmission increase will be smaller. However, even at a fraction of a percent, the transmission increase will still be detectable.

In a lithography process that uses a photomask, local changes in DUV transmission and phase attributed to the photomask may result in changes of in the size of the printed features and in the critical dimension (CD) of the circuit elements, as well as in reduced printing contrast.

One well understood mechanism of progressive degradation, described by S. Shimada et al. in "A new model of haze generation and storage life-time estimation for masks" (BACUS news, April 2007, volume 23, issue 4), is the slow growth over time of ammonium sulfate, the growth being driven by the energy due to DUV exposure. Sulfate and ammonium ions (or other monomers) may be present on or near photomask surfaces as residual contamination from previous reticle cleaning processes, from airborne molecular contamination, or from materials released from the reticle or pellicle during mask manufacture or use. A chemical reaction between the reactant ions or seed molecules may be photochemically catalyzed by DUV exposure, nucleating small particles on photomask surfaces which later grow into larger particles. Such contaminants can also grow on the surfaces of the lenses of the projection lithography tools, locally reducing their transmission and, therefore, causing optical performance to deteriorate. Once contamination has grown to a critical threshold on the photomask, the pellicle must be removed, the mask cleaned, and a new pellicle reapplied prior to reuse of the photomask. When the mask cannot be cleaned, or fails to meet specifications after cleaning, the mask must be remade.

Another phenomenon, described by Tchikoulaeva et al. in "ACLV Degradation: Root Cause Analysis and Effective Monitoring Strategy" (Proc. of SPIE, PMJ April 2008, 7028-40) is that of the migration of chrome ions from the chrome edges of a mask to nearby clear quartz areas, creating an absorptive material comprising a mixture of $Cr_2O_3$ and Cr. This ion migration phenomenon is also enhanced by the accumulated exposure to DUV during the lithography printing process.

Haze growth and other factors causing transmission changes result in high cleaning costs, loss of productivity, and disruption of the delivery of photolithography products.

Defects in the photomask tend to grow slowly until a size threshold is reached. Once the threshold is reached, a rapid dramatic increase in the chemical haze often occurs. Failure to detect this increase immediately could result in poor performance or rejection of the integrated circuits printed on the silicon wafers. The threshold for fast growth is found to occur at a typical accumulated exposure of about 4000 Joules/$cm^2$. The threshold, however, is dependent on a number of variable factors including the level of environmental contamination, details of the photomask manufacturing process, the storage environment of the photomask, etc. Thus, the inability to detect haze growth or other transmission changes at an early stage of their development could result in a serious reduction of yield when printing wafers.

Early detection of progressive changes in transmission has been found to be nearly impossible with existing photomask inspection tools. These tools are not sensitive to the changes in DUV transmission and reflection during the early stages of the process, typically less than 1%. Mapping of DUV transmission with high sensitivity is becoming essential even for unpatterned photomask blanks, coated or uncoated. As design rules of ICs become smaller and smaller, even transmission variations in the range of 0.1%-0.5% across a blank or a coated mask can measurably affect performance.

A system for measuring and mapping DUV transmission is also needed for use with the resolution enhancement techniques (RET) that are employed in photolithography. RETs, such as embedded phase shift masks (EPSM) and alternating phase shift masks (APSM), modify the phase of the DUV beam either by patterning an absorber such as MoSi (with EPSM), or by etching the quartz itself (with APSM). A MoSi or other phase shifting coating causes a change in the phase of a DUV beam in that depends on the thickness of the coating. A typical MoSi coating for a lithography tool with a 193-nm laser source is designed to yield a DUV transmission of 6%, equivalent to a phase shift of $\pi$ (180°), relative to the fused silica substrate.

By measuring DUV transmission across a photomask and mapping it, a phase variation map can be generated by converting the transmission map to a map of optical thickness variation. Relative optical thickness is related to transmission by Beer's law for absorptive layers. Since phase change is a linear function of the optical thickness, the optical thickness, and therefore the transmission, can be converted to a phase shift. The thickness of a MoSi coating required to attain a phase shift of $\pi$ at a printing wavelength of 193-nm is typically 70 nm. Such a coating transmits about 6% of the DUV incident beam. If other values of transmittance are required, other coating layers, such as $SiO_2$ or $Ta_2O_5$, may be applied to the photomask in order to attain the required transmission and phase changes. DUV transmission mapping can therefore be translated into maps of phase and CD variations.

Transmission and phase changes due to contamination may occur suddenly, for example, after cleaning the mask. If the thickness of a MoSi or $SiO_2$ layer changes by less then one percent during cleaning, phase and transmission changes could change the CD by more than 1 nanometer. Such small transmission variations in photomask blanks have also been observed, with larger variations observed in reclaimed masks that have had their pattern and coatings stripped away for reuse. Inspection tools based on optical image processing are not able to detect such small variations, where the change in transmission is less than 1%. Such tools typically employ imaging devices with small dynamic ranges, such as CCD cameras. Such imaging devices also typically have small fields of view that do not permit the statistical averaging needed to obtain a signal that exceeds the noise level.

Other fast optical methods, such as ellipsometry and scatterometry, can only be used to detect haze defects or tiny transmission variations where the defects take the form of thin films or other well-defined geometrical structures. However, as described by Jong Min Kim et al. in "Threshold residual ion concentration on photo-mask surface to prevent haze defects" (Photomask technology, Proceedings of SPIE, volume 6349, October 2006), such defects generally are not agglomerated into films or large particles during early stages of defect formation, but rather consist primarily of scattered particles of very small size, on the order of less then 100 nm.

Scanning electron microscopy (SEM) or Auger electron spectroscopy (AES) may be used to detect haze or other sources of transmission changes. However, such methods cannot be used to map a full-sized mask due to their slow speed and small field size. Such methods may only be used to examine defects after they have been detected and their locations determined. In addition, these techniques are destructive, requiring removal of the pellicle, thus obviating the need for the inspection.

One method of local transmission measurement was suggested by U.S. Pat. No. 7,251,033 (Phan et al). This patent describes in situ measurements on a reticle that is located inside a photolithographic exposure tool. However, the method is only able to measure clear areas on the mask surface, and cannot map the full active area of the mask. The method is also limited by its utilization of the light source of the lithographic exposure tool, which is a coherent monochromatic source with a noise level as high as 1%. Therefore, this method cannot detect defects at early stages of their growth, where measurement of transmission with accuracy within a fraction of a percent is required.

Another method, described by U.S. Pat. No. 6,614,520 (Bareket et al), detects defects that result in scattered light. This method involves capturing an image of the light scattered by a known good reticle, and comparing the image pixel by pixel with images captured from the reticle at later times. An algorithm is suggested for determining the thresholds of changes in light intensity that are to be used in identifying defects. This method is sensitive to individual features of the mask, and requires the scanning and detection of individual features on the reticle in order to enable distinguishing between defects and features.

It is an object of the present invention to provide a method and apparatus for metrological transmission mapping of an object that is at least partially transparent to DUV, such as for example a patterned photomask, a blank substrate (e.g. fused silica substrate) and a MoSi coated blank, in order to detect irregularities in the transmittance of DUV through the object or changes in the transmittance, indicative of defects that need fixing.

Another object of the present invention is to provide such method and apparatus in which the actual detailed features (e.g. specific pattern on a photomask) of the object are not specifically imaged, rendering the detection of transmission irregularities or transmission changes and their evaluation simpler than in methods and systems that are concerned with the details.

SUMMARY OF THE INVENTION

There is thus provided, in accordance with some embodiments of the present invention, an apparatus for transmittance mapping of an object which is at least partially transparent to deep ultraviolet radiation, the apparatus comprising:

a radiation source to generate a wide-band deep ultraviolet incoherent radiation;

optics to direct the wide-band deep ultraviolet radiation so as to illuminate areas of an array of successive areas of the object;

an optical detector positioned on an opposite side of the object with respect to the radiation source so as to detect the wide-band deep ultraviolet radiation that emerges from the object;

a relative displacement arrangement so as to facilitate relative displacement between the object and the detector or between the object and the radiation; and a processor to process signals from the optical detector.

Furthermore, in accordance with embodiments of the present invention, the optics comprises non-imaging optics.

Furthermore, in accordance with embodiments of the present invention, the relative displacement arrangement comprises an X-Y stage.

Furthermore, in accordance with embodiments of the present invention, the relative displacement arrangement comprises displacement arrangement for displacing the detector relative to the object.

Furthermore, in accordance with embodiments of the present invention, the relative displacement arrangement comprises redirecting optics for redirecting the radiation onto different areas of the array of successive areas.

Furthermore, in accordance with embodiments of the present invention, the radiation source is selected from a group of radiation sources that includes xenon, mercury-xenon and deuterium discharge lamps.

Furthermore, in accordance with embodiments of the present invention, the radiation source comprises a radiation source for generating radiation of wavelengths in the range of 180 nm to 290 nm.

Furthermore, in accordance with embodiments of the present invention, the optics comprises optics for concentrating the radiation on the predetermined area of the object.

Furthermore, in accordance with embodiments of the present invention, the detector comprises a detector selected from a group of detectors that includes: fast photodiodes, photomultiplier tubes and phototubes.

Furthermore, in accordance with embodiments of the present invention, the apparatus further comprises non-imaging optics for concentrating the radiation that emerges from the object onto the detector.

Furthermore, in accordance with embodiments of the present invention, the apparatus further comprises an imaging system.

Furthermore, in accordance with embodiments of the present invention, the detector has a wide dynamic range of 2.5 or more orders of magnitude.

Furthermore, in accordance with embodiments of the present invention, there is provided a method for transmittance mapping of an object which is at least partially transparent to deep ultraviolet radiation, the method comprising:

directing a wide-band deep ultraviolet incoherent radiation so as to illuminate different areas of an array of successive areas of the object;

using an optical detector positioned on an opposite side of the object with respect to the radiation source detecting the wide-band deep ultraviolet radiation that emerges from the object; and processing signals from the optical detector to determine the transmittance of the radiation through the different areas of the array of successive areas of the object.

Furthermore, in accordance with embodiments of the present invention, the object comprises a photomask.

Furthermore, in accordance with embodiments of the present invention, the photomask comprises a patterned photomask.

Furthermore, in accordance with embodiments of the present invention, the lateral dimensions of the different areas of the array of successive areas are greater in at least two orders of magnitude than the lateral dimension of a detail of the pattern on the patterned photomask at the different areas of the array of successive areas.

Furthermore, in accordance with embodiments of the present invention, the method is performed periodically to determine changes in the transmittance.

Furthermore, in accordance with embodiments of the present invention, the method further comprises providing relative displacement between the detector and the object.

Furthermore, in accordance with embodiments of the present invention, the method further comprises providing relative displacement between the object and the radiation.

Furthermore, in accordance with embodiments of the present invention, the radiation comprises radiation of wavelengths in the range of 180 nm to 290 nm.

Furthermore, in accordance with embodiments of the present invention, the method further comprises imaging the object for aligning the object with respect to known coordinates.

Furthermore, in accordance with embodiments of the present invention, the detector has a wide dynamic range of 2.5 or more orders of magnitude.

Furthermore, in accordance with embodiments of the present invention, a reference set of transmittance measurements for the different areas of the array of successive areas of the object previously obtained is used for comparing current transmittance through the different areas with the reference set of measurements.

Furthermore, in accordance with embodiments of the present invention, the method further comprises issuing an alert when the transmittance through at least one of different areas is below a predetermined threshold.

Furthermore, in accordance with embodiments of the present invention, the method further comprises issuing an alert when the transmittance of the radiation through the different areas of the array of successive areas of the object is below a predetermined threshold.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF EMBODIMENTS

According to embodiments of the present invention method and apparatus are provided for metrological mapping of transmittance of an object that is transparent to deep ultraviolet (DUV) radiation. For the purpose of this description, an object is considered to be transparent to DUV radiation if at least part of the object at least partially transmits DUV radiation, such that if DUV radiation is incident on a surface of that part of the object, at least part of the incident DUV radiation emerges from a different surface of the object. An example of an object that is transparent to DUV radiation is a photomask on a fused silica substrate. Although the description below refers primarily to the mapping of a photomask, it should be understood that mapping of a photomask blank (e.g. bare substrate or coated substrate), lens, or any other object that is at least partially transparent to DUV radiation is within the scope of the present invention.

The method and apparatus enable the early detection of haze and other contaminants or transmittance irregularities that form on or within the pellicle of a photomask, between the pellicle and the patterned mask, or on or within the mask itself. DUV incoherent radiation from a wide-band source is directed onto successive areas on the photomask. Each irradiated area of the photomask includes a large number of mask features (pattern features). A set of measurements of the transmission of the DUV radiation through the photomask at the successive areas is acquired, and a map of DUV transmission through the successive areas of the photomask or lens is generated and saved. At a later time, another DUV transmission map is generated. Comparison of a later map with an earlier map may indicate that significant changes in DUV transmission have occurred. Such changes in DUV transmission may indicate the presence of contaminants in the photomask or lens. Changes in transmittance above a specific threshold may indicate the need for repairing the photomask (e.g. subjecting the photomask to a repair method such as described, for example, in US patent application publication US 2005/0084767 incorporated herein by reference, or to other repairing methods).

In embodiments of the present invention, the size of the measured area at each measurement point on the photomask may cover numerous (e.g. hundreds or thousands) photomask features. The measured transmission at a measurement point then represents the average transmission of the features covered by the measured area. A set of transmission measurements covering the entire active area of the photomask may then be acquired and mapped in much less time than would an imaging scan of the same area for a feature-by-feature analysis. Fast transmission mapping of the photomask enables the measurement process to be repeated at frequent intervals. Repetition at frequent intervals, in turn, enables the early detection of haze growth and other progressive changes in transmission.

Transmission mapping is performed using incoherent wide-band DUV transmission measurements. Wide band transmission measurements enable measurement of the entire active area of the photomask using a single radiation source, regardless of the type, density, or relative transmission of the pattern. The maps of wide-band DUV transmission changes may be expected to be sensitive to all progressive processes, including the growth of haze contaminants on the surface of a reticle or on its coatings.

Embodiments of the present invention employ DUV radiation from an ultra-stable, wide-band incoherent source. The measurement spectral band is typically within the range of 180 nm to 290 nm. This band includes the two most widely used exposure wavelengths in advanced lithography: 193 nm from ArF excimer laser sources and 248 nm from KrF excimer laser sources. Suitable DUV radiation sources include, but are not limited to, xenon (Xe), mercury-xenon (HgXe), and deuterium ($D_2$) discharge lamps.

DUV radiation is directed into the photomask from either the back or front side of the reticle. A non-imaging optical system directs and concentrates the radiation near the pattern layer. In embodiments of the present invention, the photomask is irradiated by DUV radiation through the back side of the substrate. An optical system directs the radiation so as to illuminate the mask on the front surface of the reticle. A typical diameter of the illuminated spot may be in the range of 0.1 mm to 5.5 mm.

DUV radiation that traverses the photomask and emerges through the opposite surface (or other surface, if some deflection occurs) is detected. When illuminated through the back side of the substrate, radiation emerging from the front side is detected. In embodiments of the present invention, the detection system that detects the emerging DUV radiation includes a single detector. The detector produces a signal that corresponds the intensity of the radiation incident on a radiation detection component of the detector. No further detectors are needed since there is no need to create an image. The radiation detection component of the detector may be a fast photodiode, a photomultiplier tube (PMT), a phototube, or any other device adaptable to detecting and measuring DUV radiation. The detection system may include non-imaging collection optics for concentrating the emerging radiation onto the radiation detection component.

In embodiments of the present invention, the detector has a wide dynamic range of 2.5 or more orders of magnitude. The large dynamic range enables the detector to achieve a very large signal-to-noise ratio (SNR). Since a single measurement may be acquired in only a fraction of a second, several repeated measurements may be averaged to increase further increase the SNR. In this manner, at the cost of increasing the measurement time by an amount that generally would not be considered excessive, measurement accuracy to within 0.1% may be achieved. This high level of accuracy is possible since the available irradiance may exceed 500 $\mu W/cm^2$, while the noise equivalent power (NEP), mainly the result of dark current, is less then 1 $nW/cm^2$.

In embodiments of the present invention, the high accuracy of the transmission variation measurements may enable extraction of information regarding phase changes caused by progressive defects. The extraction of phase-change information would be possible where there has been a separate determination of the index of refraction of the defect material, and where optical thin film effects take place.

In embodiments of the present invention, measurement over the full photomask is accomplished by a relative displacement arrangement. The relative displacement arrangement causes relative translation between the mask and the DUV illumination in an X-Y plane that is normal to the direction of incidence of the DUV radiation on the mask. Translating the photomask in the X-Y plane successively aligns all parts of the mask with the incident DUV radiation and the detection system. Translation of the photomask may be performed using a movable X-Y stage. The motion of the X-Y stage may be in the form of a discrete step-and-repeat motion, or a continuous raster scan.

Alternatively, instead of translating the photomask, the photomask may be held stationary while the DUV illumination system and the detection system move across the photomask. Alternatively, the detection system may be capable of detecting the radiation that emerges from all portions of the photomask. For example, the detector may include a single large radiation detection component extending across the entire object. In this case, both the photomask and the detector may remain stationary, while successive areas of the photomask are illuminated with DUV radiation.

Coordinates of the points during the X-Y motion at which measurements are made, and the results of the set of measurements made at those points, are input to a central computer unit. On the basis of the measurement set and the coordinate data that are input, the central computer unit generates a map of the transmission values.

Measurement set acquisition and mapping operations are repeated periodically on a photomask. The criteria for determining when a measurement is to be performed may take into account the cumulative exposure of the photomask to DUV, the number of wafers printed using the mask in IC production, performance of a cleaning process on the mask, or any other suitable criteria. Each measurement set and map is stored in the memory of the central computer unit. A measurement set is compared to a previous measurement set, and a map of the differences in transmission values is generated. In this manner, changes amounting to a fraction of a percent in transmission from measurement set to measurement set may be detected.

The system is calibrated at predefined intervals during the acquisition of a measurement set by performing a measurement through air, rather than through the photomask. For example, such a calibration measurement may be performed after a fixed number of point measurements. In this manner, the output of the detection system can be corrected for drift in detector sensitivity using air as a reference.

In embodiments of the present invention, transmission measurements are performed with the pellicle in place on the photomask. The capability of performing transmission measurements with the pellicle in place facilitates early detection of changes in DUV transmission. Since the photomask remains intact during the measurement process, the measurement may be performed in the wafer fabrication plant where the photomasks are used. Were it necessary to remove the pellicle, performing the measurement would likely entail removing the photomask from the wafer fabrication plant to a photomask manufacturing facility.

Laboratory tests were conducted in order to determine the measurement precision attainable by embodiments of the present invention. For sets of single measurements, a standard deviation less than 0.2% was attained. For averages of multiple measurement sets, where the multiple measurements were performed within a time interval of less than one second, a standard deviation less than 0.1% was attained.

Figure 1:
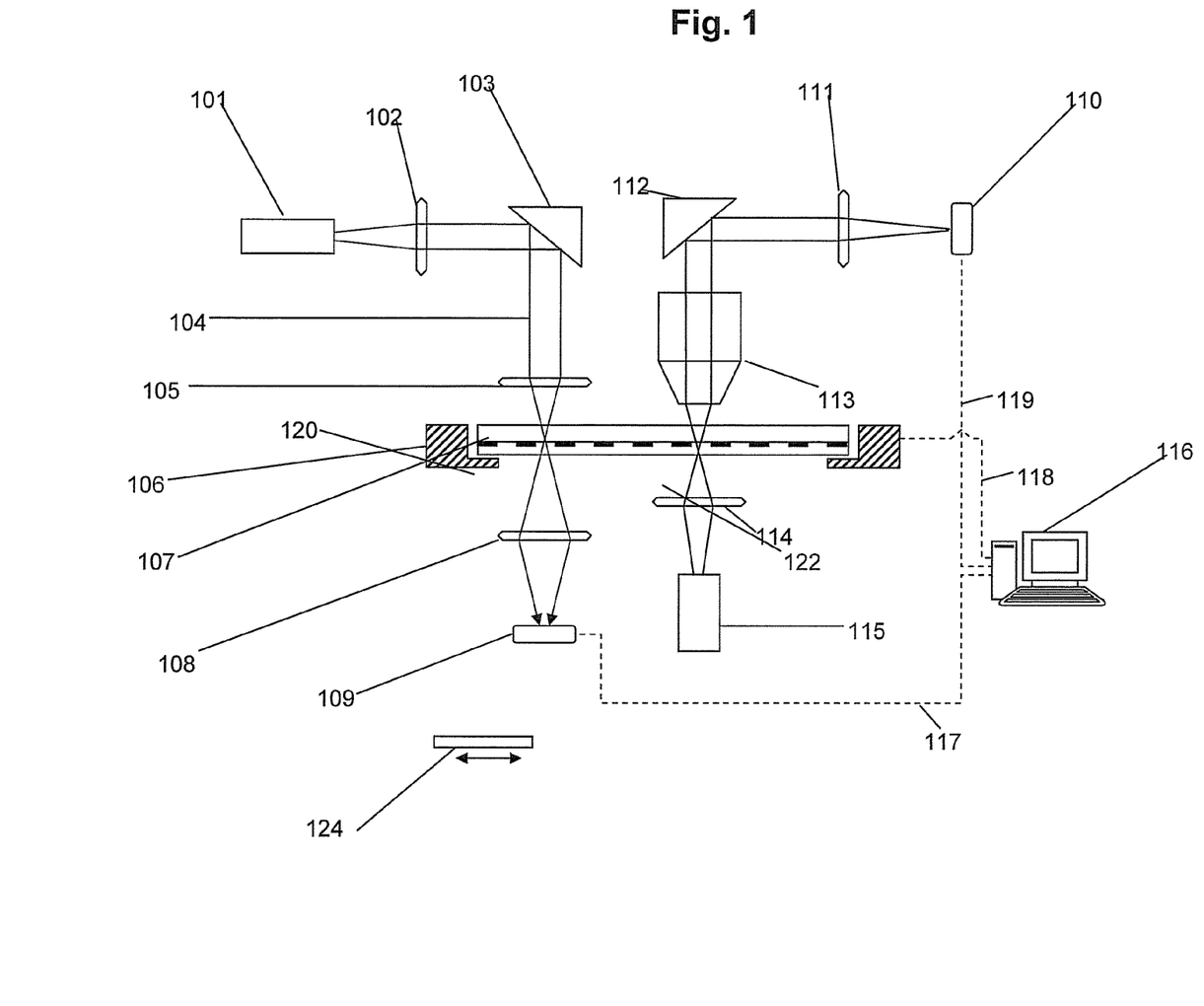
FIG. 1 is a schematic illustration of a DUV transmission mapping system in accordance with embodiments of the present invention, used in mapping transmission for a patterned photomask.

We now describe embodiments of the present invention with reference to the accompanying Figures. FIG. 1 is a schematic illustration of a DUV transmission measurement system in accordance with embodiments of the present invention.

DUV radiation 104 originates from wide-band DUV source 101. DUV radiation 104 may be collimated by a collimating optical system, represented by collimating lens 102. Optionally, DUV beam may be redirected using redirecting optics 103. A concentrating system, represented by focusing lens 105, concentrates DUV radiation 104 to illuminate an area 120 on the back side of photomask 107. Photomask 107 is installed on movable XY stage 106.

A portion of the DUV radiation that illuminates area 120 may emerge from the opposite side of photomask 107. Emerging DUV radiation is collected by a collecting optical system, represented by collecting lens 108. The collected DUV radiation is directed toward, and is incident on, DUV detector 109. DUV detector 109 is optionally mounted on detector translation stage 124. DUV detector 109 creates a signal in response to the incident DUV radiation. The created signal is transmitted via connection 117 to central computer unit 116 for data acquisition and processing. Acquisition and processing of a signal created by DUV detector 109 is referred to as a measurement.

Movable XY stage 106 translates photomask 107 in a plane substantially perpendicular to the axis of DUV radiation 104. The axis of DUV radiation 104 is essentially determined by the optical axis of focusing lens 105. The translation is such as to bring successive regions of photomask 107 to the location of illuminated area 120. As each successive region of photomask 107 is brought to the location of area 120, a measurement is made. The translation of photomask 107 is controlled by computer unit 116 through connection 118. The controlled translation of photomask 107 is such that at the conclusion of the measurement process, a set of measurements will have been performed covering the entire active area of photomask 107.

Alternatively, photomask 107 remains stationary while redirecting optics 103 causes DUV radiation 104 to illuminate successive areas of photomask 107. Detector translation stage 124 moves detector 109 such that detector 109 detects the DUV radiation that emerges from the illuminated area of photomask 107.

An imaging system is provided to determine the position of illuminated spot 120 on photomask 107. Light originating from light source 115 is focused by condenser lens 114 to spot 122 on photomask 107. An optical system may include objective lens 113 and tube-lens 111. If necessary, the optical axis of the optical system may be redirected using redirecting optics 112. The optical system creates an image of that region of photomask 107 that is illuminated by spot 122 on CCD camera 110.

Photomask 107 is provided with alignment marks at fixed locations on photomask 107. The alignment marks are visible by the imaging system. CCD camera image data is transmitted to computer unit 116 via data link 119. The CCD image data is processed by computer unit 116. Processing of the CCD image data determines when an alignment mark is located at spot 122. The location of spot 122 is fixed in space relative to the location of illuminated area 120. Therefore, when the imaging system determines that an alignment mark is located at spot 122, a corresponding region of photomask 107 is reproducibly located at illuminated area 120. In this way, a reproducible coordinate system on the surface of photomask 107 is established. Communication between computer unit 116 and moveable XY stage 106, the measurement system, and the imaging system, enables the determination of the coordinates of each transmission measurement of the measurement set. In this way, computer unit 116 is able to map the transmission over the surface of photomask 107.

Figure 2:
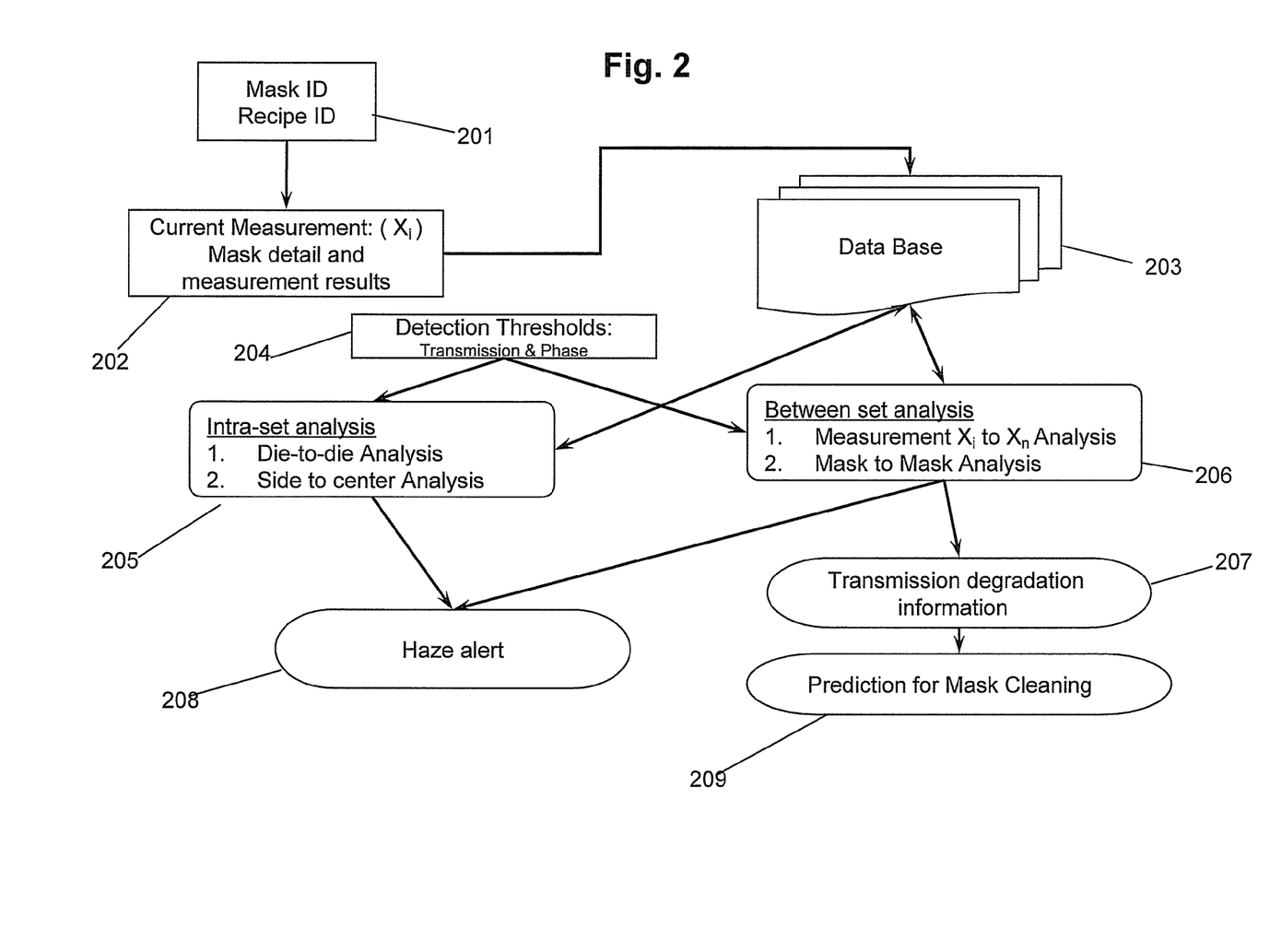
FIG. 2 is a block diagram of the operation of the system illustrated in FIG. 1.

FIG. 2 is a block diagram of the operation of the system illustrated in FIG. 1. Parameters 201 defining a photomask and the associated recipe, or measurement protocol, are input to the system. The photomask to be tested is placed in the measurement system. The measurement system performs a measurement process on the photomask and produces a set of measurements 202. The set of measurement and imaging results is saved in a database 203.

Two types of analysis are performed. Intra-set analysis 205 compares measurement results within a single measurement set to one another. For example, measurement results for an area of a photomask blank may be compared with measurement results for another area of the same photomask blank. In another example, measurement results on one or more local areas of a photomask reticle may be compared to results on areas of the photomask reticle with identical features (die-to-die comparison). Similarly, results for local areas near the center of a photomask reticle may be compared with results for areas with identical features near the periphery of the reticle. Any differences in transmission or phase shift that are detected are compared with stored detection thresholds 204. Should differences that exceed detection thresholds 204 be detected, the system issues an alert 208 to the presence of contamination on the photomask. The significance of such an alert is that the photomask should be removed from use in photolithography until it is cleaned.

Inter-set analysis 206 compares results from one measurement set with results from another. Results of a measurements performed on a photomask on one date may be compared with the results of measurement performed on the same photomask on a different date. For example, measurements made prior to use in photolithography would be compared with measurements made after a period of use. Alternatively, measurements made on one photomask could be compared with measurements made on an identical mask. For example, measurement results for a photomask that was used in photolithography may be compared with another identical one that was never used. Again, any differences detected are compared with the stored detection thresholds 202. When detected differences exceed detection thresholds 204, the system issues an alert 208 to the presence of haze or other contamination on the photomask. Alternatively, should detected differences not exceed detection thresholds 204, the system may generate transmission degradation information 207. On the basis of transmission degradation information 207, a prediction 209 may be made as to when the transmission of the photomask should be measured again, or when the photomask should be cleaned.

FIGS. 3-5A illustrate phases of progressive transmission loss through a photomask. Although, for the sake of illustration, defects are shown forming on the front surface of the mask, defects may in fact form on any surface of the mask.

Figure 3:
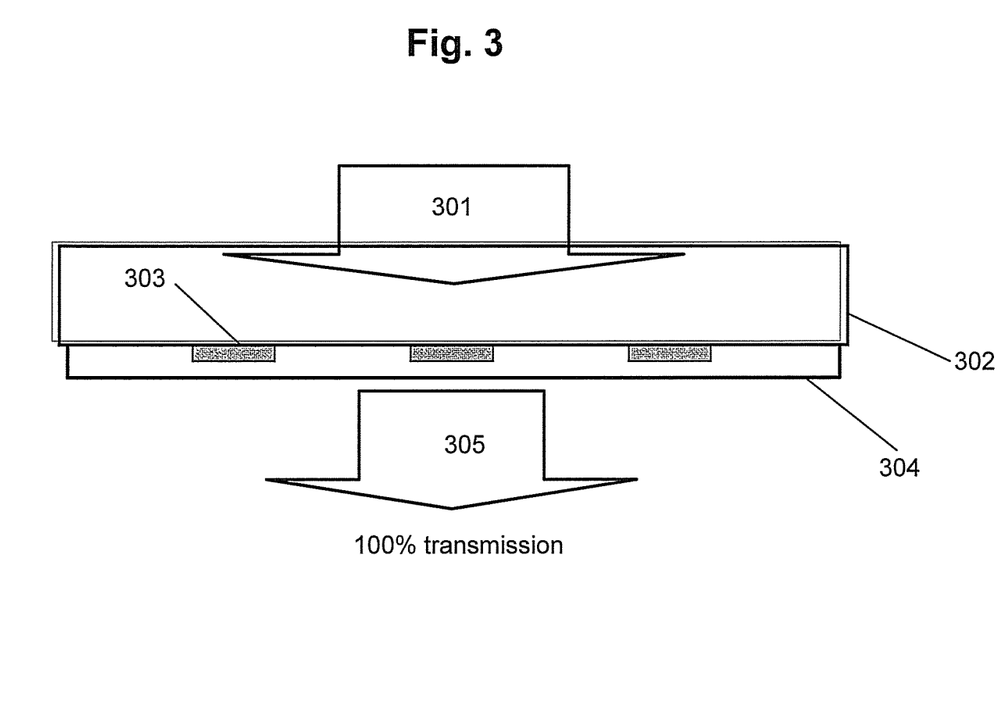
FIG. 3 is a schematic illustration of DUV radiation transmission through a newly patterned photomask.

FIG. 3 is a schematic illustration of DUV radiation transmission through a newly patterned photomask. An incoming DUV beam 301 uniformly illuminates mask surface 303 through substrate 302. Mask pattern 303 consists of a patterned absorber, such as chrome or MoSi, on quartz substrate 302. Beam 305 emerges from the photomask with its intensity reduced by reflections at interface surfaces, by blocking by mask pattern 303, and by absorption and scattering within substrate 302. At this point, however, there are no defects or contaminants on mask surface 303 or on protective pellicle 304. Therefore, beam 305, which emerges from the mask side of photomask, is described as being transmitted with 100% relative transmission.

Figure 4:
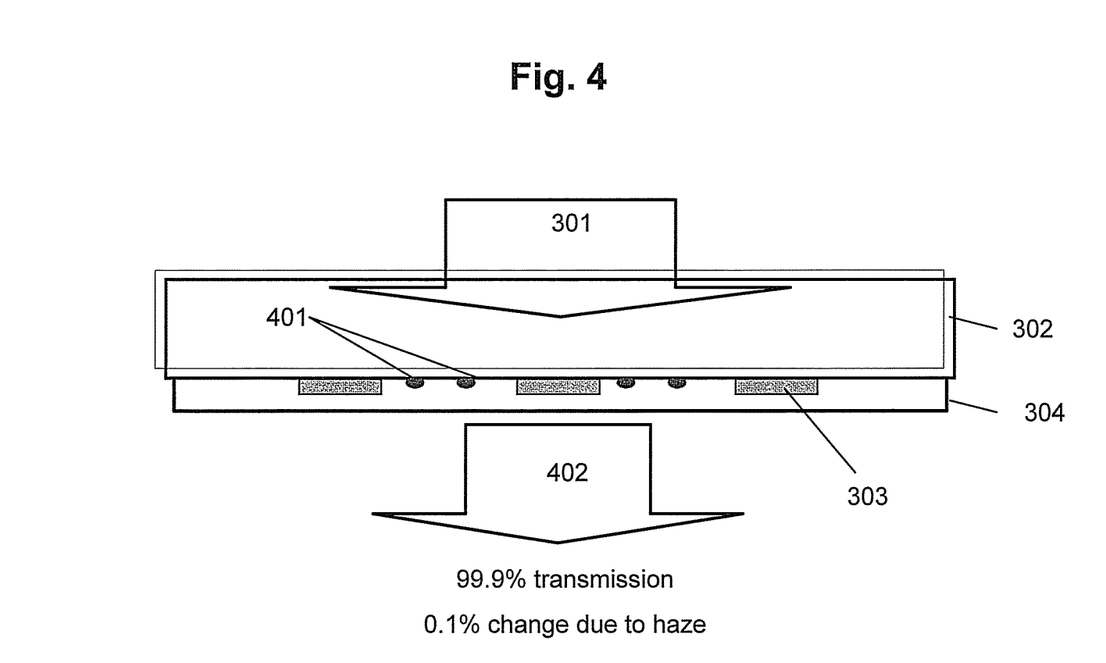
FIG. 4 schematically illustrates a small reduction in DUV transmission through a photomask.

FIG. 4 schematically illustrates a small reduction in DUV transmission through a photomask. In this phase of progressive transmission loss, haze contaminants 401 have started to grow on the front surface of the mask. At this point, however, the change in transmission is measurable, but still small. In the example shown, DIN beam 402 emerges from the mask with a relative intensity of 99.9% of the intensity of beam 305 (FIG. 3) that emerges when no contaminants are present. The transmission loss is 0.1%. Typically, when the loss in transmission is small, the photomask may continue to be used for photolithography.

Figure 5A:
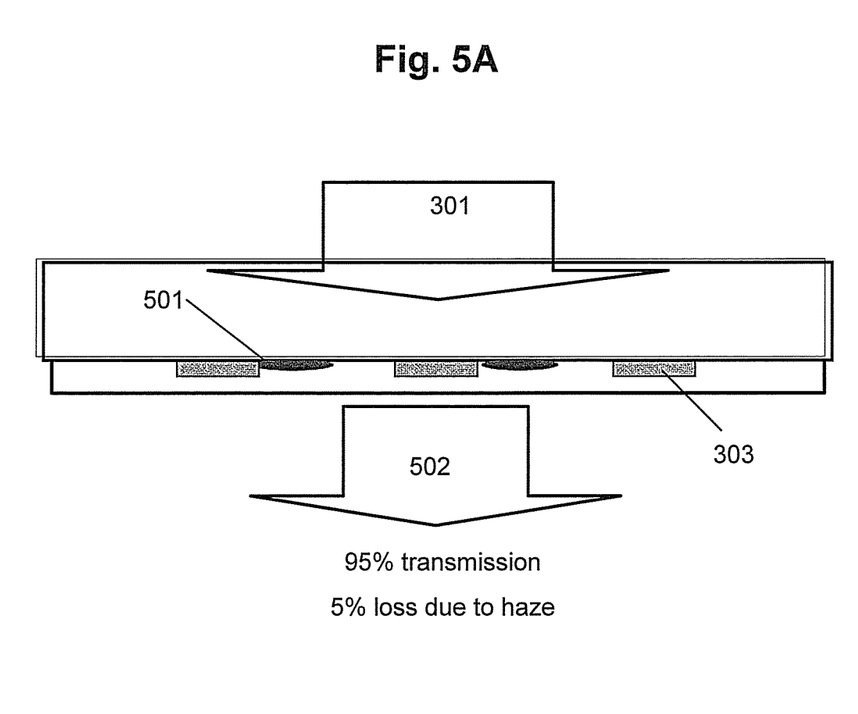
FIG. 5A schematically illustrates an unacceptable loss in transmission through a photomask.

FIG. 5A schematically illustrates an unacceptable loss in transmission through a photomask. In this phase of progressive transmission loss, the transmission loss due to the contaminant growth 501 on the mask surface 501 exceeds an acceptable threshold. In the example shown, beam 502 emerges with an intensity that is 95% of that of beam 305 (FIG. 3). Such a transmission loss renders the photomask unsuitable for use in photolithography. In order to be used, a photomask with such a transmission loss must either be cleaned or discarded.

Figure 5B:
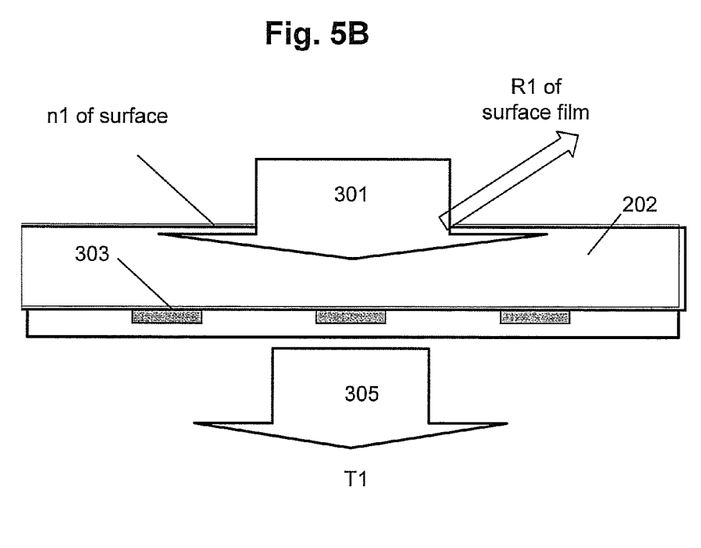
FIG. 5B schematically illustrates reflection and transmission from an uncontaminated photomask surface.
Figure 5C:
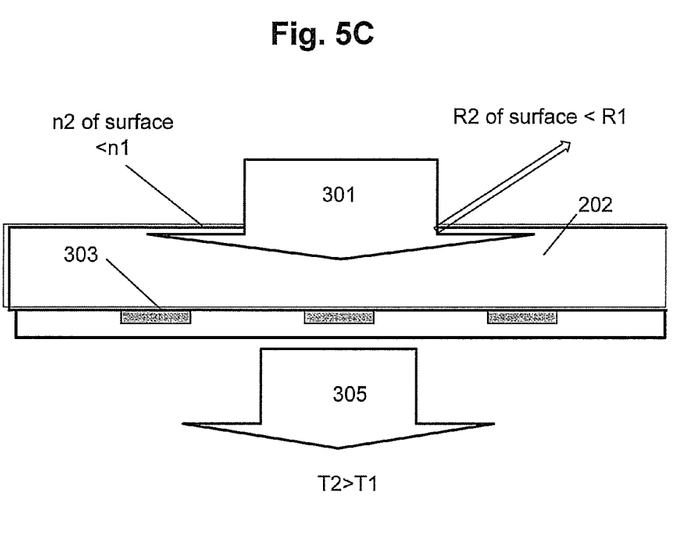
FIG. 5C schematically illustrates an example of reflection and transmission from a photomask surface after exposure to DUV.

FIG. 5B and FIG. 5C illustrate an example of the effects of thin film growth on a surface of a photomask. FIG. 5B schematically illustrates reflection and transmission from an uncontaminated photomask surface. DUV beam 301 is normally incident on the surface of substrate 302. A portion R1 of the incident radiation is reflected. R1 is determined by index of refraction n1 of the quartz substrate. The fraction T1 of the incident radiation that is transmitted in the form of beam 305 is determined by the value of R1, the properties of mask 303, and absorption or scattering effects within the various components of the photomask. FIG. 5C schematically illustrates an example of reflection and transmission from a photomask surface after exposure to DUV. After exposure to DUV radiation during photolithography, the index of refraction of a layer of substrate material near the surface of substrate 302 may be modified to n2. In the example shown, n2 is smaller then substrate index of refraction n1. In this case, the fraction R2 of the incident radiation that is reflected by the substrate with the modified surface layer may be less than R1. Therefore, in the case of this example, the result is an increase in the intensity T2 of transmitted beam 305, relative to intensity T1.

Figure 6:
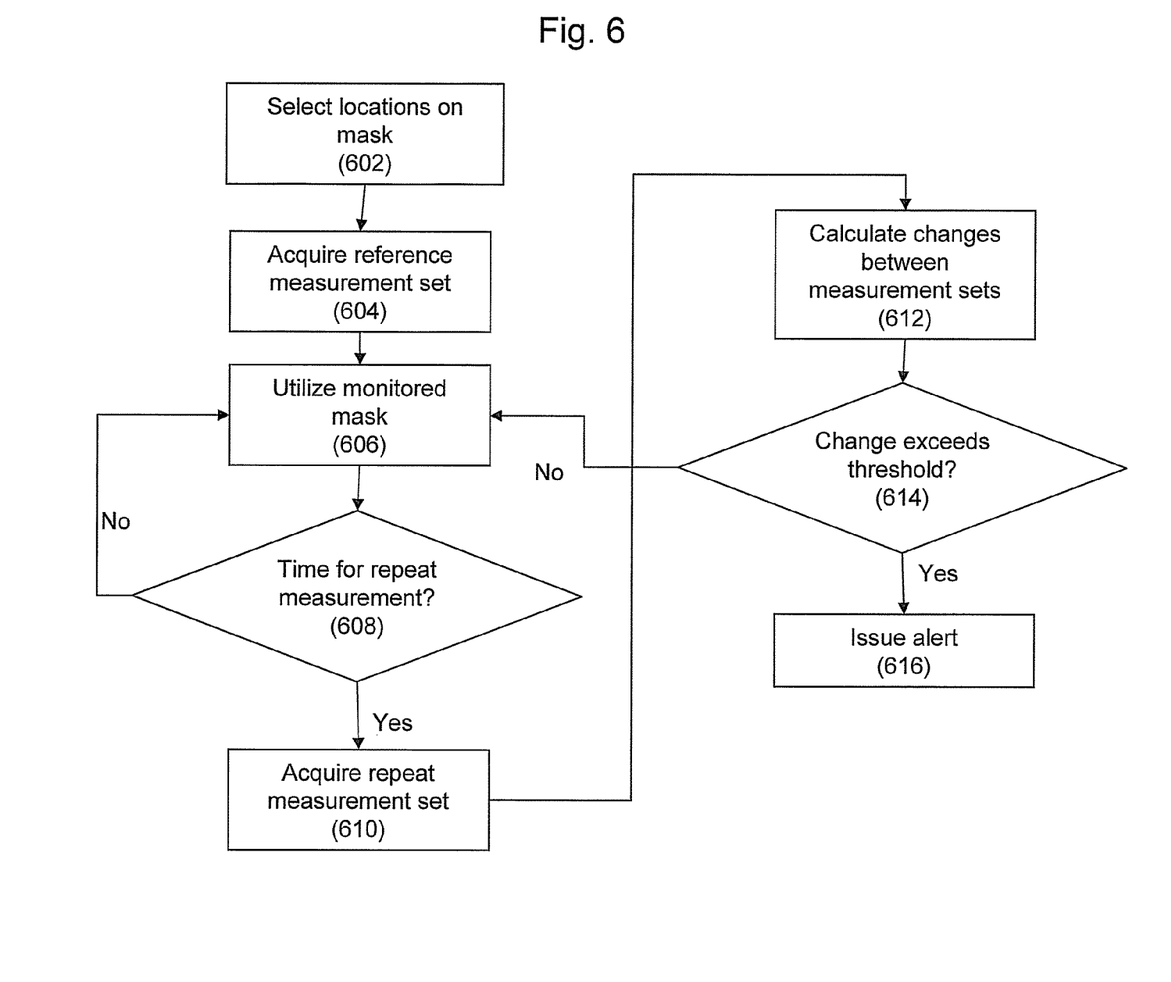
FIG. 6 is a flow chart of a method for detecting changes in transmission in accordance with embodiments of the present invention.

In accordance with embodiments of the present invention, a method is provided for monitoring DUV transmission by applying detection rules for automatically detecting contamination on a photomask. FIG. 6 is a flow chart of a method for detecting changes in transmission in accordance with embodiments of the present invention. Predefined measurement locations are selected on the mask (step 602). The locations may be chosen arbitrarily, for example, evenly spaced to cover the entire mask surface. Alternatively, the locations may be selected based on prior knowledge of typical transmission change behavior or of the mask layout. For example, previous experience may show that a chemical haze initially grows inward from the periphery of the mask. In such cases, the measurement points may be chosen with a higher density in the periphery, and with a lower density near the center.

As a first step of the monitoring process, reference measurements are made at the predefined locations on the specific mask to be monitored (step 604). The reference measurements are made on the mask shortly after manufacture or cleaning, prior to its use in photolithography. The reference measurement results Tr0 are saved for comparison with measurements made at a later date.

Alternatively, the reference measurements may be made on a similar mask of the same design as the mask to be monitored. However, unlike the monitored mask, the reference mask is not exposed to DUV radiation as part of a photolithographic process. The reference mask is stored for later use in reference measurements. This alternate method of comparing measurements on different masks is referred to as a mask-to-mask reference method. The reference measurements on the reference mask are repeated to create reference measurement results Tr0 whenever measurements are made on the monitored mask. Therefore, with the mask-to-mask method, reference measurement results need not be stored for an extended period of time.

The set of reference measurements Tr0 represents a reference transmittance measurement map. Optionally, each transmittance measurement of the reference set may be defined as a difference or delta from the average of the set of measurements, labeled DTM0 for delta transmission map. DTM0 or Tr0 may be based on a set of single measurements on each point of the photomask, or may be based on an average of several repetitions of the same set of measurements.

The monitored mask may be used in a lithographic process, where it is exposed to a high energy light source, such as a 193-nm or 248-nm excimer laser (step 606). Measurements on the mask are repeated after the mask has been used for a predefined period of time, has been exposed to a predefined cumulative exposure dose, or after meeting any other criteria defined as indicating that measurements on the mask are to be repeated (step 608). The criteria for determining when measurements are to be repeated may be based on experimentally determined rates of growth of known modes of transmission loss, scheduled cleaning intervals, or other factors. The criteria may vary dependent upon other factors. For example, measurements may be repeated more frequently after the measured transmission drops below a certain value if it is known that the rate of transmission loss increases after reaching that value.

A set of repeat measurements (step 610) may be labeled Trx or DTMx, where x represents the number of the measurement set. As with the reference measurements, the repeat measurements are also made at the predefined locations on the mask. Alternatively, new locations may be measured in addition to the predefined reference locations. After a set of measurements is repeated, the system applies an automatic comparison algorithm. The automatic comparison algorithm compares the set of repeated measurements to the set of reference measurements.

The comparisons are divided into two basic types. In the first type, a current set of measurements, Trx or DTMx, may be compared to the set of reference measurements Tr0 or DTM0, or to any other previous set of measurements. For each measurement made at one of the predefined locations, the difference or ratio between the current measurement and the reference measurement is calculated.

In the second basic type of comparison, a measurement at a location on a photomask reticle is compared with a measurement made at another location on the same reticle. The two locations of the reticle that are being compared have identical features, i.e., the same chip design at different locations on the mask. For example, the two locations may be located on adjacent dice of the reticle. In another example, one location is near the center of the reticle, while the other is at the periphery.

The comparison algorithm compares the calculated measurement-to-measurement differences or ratios to predefined detection thresholds for transmittance change, and, in some cases, for, phase change (step 612). Differences may be divided by a transmittance value to yield a relative change, expressed as a fraction or in percent. The threshold is defined as a minimum detectable loss in transmittance, or change in phase, between different measurements. When the comparison value is larger than the threshold value (step 614), the system alerts the user of transmission loss at the location (step 616). Detected transmission changes that are systematic over several measurement locations may indicate changes due to one or more of the types of contamination described above.

A non-systematic detected transmission change, for example, a change detected at a measurement single point, may indicate localized particle contamination. However, it could also possibly indicate a measurement error.

Sets of measurements are organized in a database. Data associated with a saved measurement set in the database may include: mask identification, serial number, layer identification, technology, date of manufacture, and other data by which the measurement sets may be categorized. The database also enables tracking of the number of times a mask is exposed to DUV radiation and the cumulative radiation exposure dose on the mask. The database algorithm utilizes the cumulative dose and transmittance or phase change information to predict when the mask should be sent for cleaning, review, or to be remade.

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the present invention.

The invention claimed is:

1. A method for transmittance mapping of a photomask which is at least partially transparent to deep ultraviolet radiation, the method comprising:
    directing a wide-band deep ultraviolet incoherent radiation so as to illuminate different areas of an array of successive areas of the photomask;
    using a non-imaging optical detector with a wide dynamic range of 3 or more orders of magnitude and that is positioned on an opposite side of the photomask with respect to the radiation source to detect the wide-band deep ultraviolet radiation that is transmitted by the photomask and that emerges from the opposite side of the photomask;
    processing signals from the optical detector to determine the transmittance of the radiation through the different areas of the array of successive areas of the photomask; and
    repeating determination of the transmittance to determine changes in the transmittance so as to monitor degradation of the photomask.

2. The method as claimed in claim 1, wherein the photomask comprises a patterned photomask and the lateral dimensions of the different areas of the array of successive areas are greater in at least two orders of magnitude than the lateral dimension of a detail of the pattern on the patterned photomask at these different areas.

3. The method as claimed in claim 1, further comprising providing relative displacement between the detector and the photomask.

4. The method as claimed in claim 1, further comprising providing relative displacement between the photomask and the radiation.

5. The method as claimed in claim 1, wherein the radiation comprises radiation of wavelengths in the range of 180 nm to 290 nm.

6. The method as claimed in claim 1, further comprising imaging the photomask for aligning the photomask with respect to known coordinates.

7. The method as claimed in claim 1, wherein a reference set of transmittance measurements for the different areas of the array of successive areas of the photomask previously obtained is used for comparing current transmittance through the different areas with the reference set of measurements.

8. The method as claimed in claim 7, further comprising issuing an alert when the transmittance of the radiation through the different areas of the array of successive areas of the photomask is below a predetermined threshold.

9. The method as claimed in claim 7, wherein the reference set of transmittance measurements comprises measurements of an area of the photomask that has optical features that are repeated in other areas of the photomask.

10. The method as claimed in claim 7, further comprising issuing an alert when the transmittance through at least one of the different areas is below a predetermined threshold.

11. The method as claimed in claim 1, further comprising performing air-calibration.

12. The method as claimed in claim 1, wherein the degradation comprises growth of a contaminant on the photomask or a change in index of refraction of a part of the photomask.

* * * * *